(12) United States Patent
D'Souza et al.

(10) Patent No.: US 8,937,201 B2
(45) Date of Patent: Jan. 20, 2015

(54) PROCESS FOR PRODUCING A T-BUTYL PHENOL FROM A $C_4$ RAFFINATE STREAM

(75) Inventors: Roger D'Souza, Niskayuna, NY (US); Scott Smith, Schenectady, NY (US); Kirthivasan Nagarajan, Cohoes, NY (US)

(73) Assignee: SI Group, Inc., Schenectady, NY (US)

( * ) Notice: Subject to any disclaimer, the term of this patent is extended or adjusted under 35 U.S.C. 154(b) by 0 days.

(21) Appl. No.: 13/513,666

(22) PCT Filed: Dec. 3, 2010
(Under 37 CFR 1.47)

(86) PCT No.: PCT/US2010/058866
§ 371 (c)(1),
(2), (4) Date: Jan. 24, 2013

(87) PCT Pub. No.: WO2011/069052
PCT Pub. Date: Jun. 9, 2011

(65) Prior Publication Data
US 2013/0150629 A1    Jun. 13, 2013

Related U.S. Application Data

(60) Provisional application No. 61/266,828, filed on Dec. 4, 2009.

(51) Int. Cl.
*C07C 39/06* (2006.01)
*C07C 37/14* (2006.01)

(52) U.S. Cl.
CPC .................................... *C07C 37/14* (2013.01)
USPC ......................................... 568/789; 568/784

(58) Field of Classification Search
CPC ................................. C07C 37/14; C07C 39/06
USPC .................................................. 568/784, 789
See application file for complete search history.

(56) References Cited

U.S. PATENT DOCUMENTS

| 2,353,282 | A |   | 7/1944 | Turkington et al. |
| 4,260,833 | A |   | 4/1981 | Firth |
| 5,292,970 | A | * | 3/1994 | Kupper et al. ................ 568/794 |

FOREIGN PATENT DOCUMENTS

| CS | 276820 | * | 3/1992 | ............. C07C 37/48 |
| CZ | CS276820 B6 |   | 8/1992 | |
| GB | 655124 A |   | 7/1951 | |
| JP | 54-73738 A |   | 6/1979 | |
| JP | 57-95928 A |   | 6/1982 | |
| JP | 63-159333 A |   | 7/1988 | |

OTHER PUBLICATIONS

Wali et al., Disproportionation, isomerization and de-tert-butylation of 2,6-di-tert-butylphenol catalyzed by H-MCM-41, Green Chemistry, 4, 587-591, 2002.*

* cited by examiner

*Primary Examiner* — Paul A Zucker
*Assistant Examiner* — Mark Luderer
(74) *Attorney, Agent, or Firm* — Jeffrey N. Townes; LeClairRyan

(57) ABSTRACT

This invention relates to processes for producing various t-butyl phenols, such as 2,6-di-tert-butyl phenol and ortho-tert-butyl phenol, by selectively reacting phenol or a substituted phenol with an isobutylene-containing $C_4$ raffinate stream. The 2,6-di-tert-butyl phenol and ortho-tert-butyl phenol can be transalkylated to form other tert-butyl phenols, such as para-tert-butyl phenol, 2,4-di-tert-butyl phenol.

25 Claims, No Drawings

PROCESS FOR PRODUCING A T-BUTYL PHENOL FROM A C$_4$ RAFFINATE STREAM

CROSS REFERENCE TO RELATED APPLICATIONS

This application claims priority under 35 U.S.C. §119 to U.S. provisional application Ser. No. 61/266,828, filed Dec. 4, 2009, which is incorporated herein by reference.

FIELD OF INVENTION

This invention relates to processes for producing various t-butyl phenols from an isobutylene-containing C$_4$ raffinate stream.

BACKGROUND

In refining crude petroleum, various naphtha streams are produced in additional to the gasoline pool. The naphtha streams, which contain valuable compounds such as ethylene and propylene, are then often times introduced into a naphtha cracker to produce products such as polyethylene and polypropylene. The naphtha cracker, in turn, produces various streams, including a C$_4$ raffinate stream that contains isobutene, butadiene, isobutylene, and other C$_4$ molecules, many of which are also very useful. For instance, butadiene can be polymerized and used in various rubbers, and isobutylene is useful as a starting material for many industrial compounds, including tert-butyl-phenols.

However, to produce tert-butyl phenols from isobutylene typically involves a "pure" isobutylene, while the isobutylene from the raffinate stream contains varying amounts of butenes and butanes in addition to other alkanes and alkenes ranging from C$_2$ to C$_5$. When reacting the C$_4$ raffinate stream with phenol, the butenes, particularly the 1-butene and the 2-butene, competitively react with the phenol to produce undesirable sec-butyl phenols in addition to the desirable tert-butyl phenols. Separating the sec-butyl phenols from the tert-butyl-phenols is costly and adversely affects the yield the desired products.

Conventional processes for producing tert-butyl phenols from an isobutylene-containing C$_4$ raffinate stream typically involve introducing methanol, or another alcohol, into the C$_4$ stream to react create an alkyl-tert-butyl ether intermediate that is further decomposed to make high-purity isobutylene, which can then be reacted with phenol to produce the tert-butyl phenols. The additional step of adding methanol significantly increases the costs of producing tert-butyl phenols, and creates another undesirable byproduct. Besides the additional expense, the additional byproducts are unattractive for environmental reasons. Various other methods of producing tert-butyl phenols are disclosed in U.S. Pat. No. 4,166,191, but these processes, like the conventional methods, utilize extra steps and expensive materials.

What is needed in the art is a method of producing a tert-butyl phenol by selectively reacting a phenol with an isobutylene-containing C$_4$ raffinate stream so that the isobutylene reacts with the phenol while none, or very few, of the butenes present in the C$_4$ raffinate stream are reacted with the phenol. This invention answers that need.

SUMMARY OF THE INVENTION

This invention relates to a process for producing a tert-butyl phenol, such as 2,6-di-tert-butyl phenol or ortho-tert-butyl phenol that involves reacting an isobutylene-containing C$_4$ raffinate stream with a phenol or a substituted phenol in the presence of a Group IIIb metal, such as aluminum, or a Group IIIb metal oxide, such as aluminum oxide. The reaction should be run at a reaction temperature ranging from about 50° C. to about 150° C., where the molar ratio of isobutylene to phenol ranges from about 0.5:1 to about 3:1.

The invention also relates to a process for producing ortho-tert-butyl phenol that involves reacting an isobutylene-containing C$_4$ raffinate stream with a phenol in the presence of an aluminum oxide catalyst. In this process, the reaction temperature ranges from about 150° C. to about 200° C., and the molar ratio of isobutylene to phenol ranges from about 0.5:1 to about 1.5:1.

The invention also relates to a process for producing 2,6-di-tert-butyl phenol that involves reacting an isobutylene-containing C$_4$ raffinate stream with ortho-tert-butyl phenol in the presence of aluminum or aluminum trisphenoxide. In this process, the reaction temperature ranging from about 0° C. to about 30° C., and the molar ratio of isobutylene to ortho-tert-butyl phenol ranges from about 0.5:1 to about 2.0:1.

The invention also relates to a process for producing a tert-butyl phenol, such as 2,6-di-tert-butyl phenol or ortho-tert-butyl phenol, that involves reacting a phenol with a C$_4$ raffinate stream containing (a) isobutylene, and (b) 1-butene and/or 2-butene. The reaction is run under reaction conditions that selectively react the isobutylene with the phenol to produce the tert-butyl phenol without substantially reacting the 1-butene or 2-butene with the phenol.

The invention also relates to a process for producing a tert-butyl phenol directly from an isobutylene-containing C$_4$ raffinate stream without forming an alkyl-tert-butyl ether as an intermediate. In the process, the isobutylene-containing C$_4$ raffinate stream is directly reacted with a phenol to produce the tert-butyl phenol. The reaction proceeds without the intermediate step of forming an alkyl-tert-butyl ether.

The invention also relates to an alcohol-free process for producing a tert-butyl phenol directly from an isobutylene-containing C$_4$ raffinate stream. The method involves directly reacting the isobutylene-containing C$_4$ raffinate stream with a phenol to produce the tert-butyl phenol. The reaction process avoids the intermediate step of introducing an alcohol, such as methanol or amyl alcohol, into the C$_4$ raffinate stream.

The invention also relates to a composition comprising one or more tert-butyl phenols containing less than 0.5% by weight of sec-butyl phenols. The composition is prepared by directly reacting a phenol with a C$_4$ raffinate stream containing (a) isobutylene and (b) 1-butene and/or 2-butene.

DETAILED DESCRIPTION

Tert-butyl phenols are useful as starting materials for producing plasticizers, resins, spices, polymerization inhibitors, antioxidants, molecular weight regulators, and various other chemical products. Additionally, certain tert-butyl phenols are useful as fragrance or flavor compounds and may be used in a wide variety of household, personal care, and industrial items, such as perfumes, cleansers, or detergents, to impart a pleasing odor to the item.

One embodiment of the invention relates to a process for producing a tert-butyl phenol, comprising reacting an isobutylene-containing C$_4$ raffinate stream with a phenol or a substituted phenol in the presence of a Group IIIb metal or a Group IIIb metal oxide at a reaction temperature ranging from about 50° C. to about 150° C., wherein the molar ratio of isobutylene to phenol ranges from about 0.5:1 to about 3:1. This embodiment includes, for instance, a process for producing a tert-butyl phenol, comprising reacting an isobutylene-containing $C_4$ raffinate stream with a phenol or a substituted phenol in the presence of a Group IIIb metal or a Group IIIb metal oxide at a reaction temperature ranging from about 50° C. to about 150° C., wherein the molar ratio of isobutylene to phenol ranges from about 0.5:1 to about 2.5:1. This embodiment also includes, for instance, a process for producing a tert-butyl phenol, comprising reacting an isobutylene-containing $C_4$ raffinate stream with a phenol or a substituted phenol in the presence of a Group Mb metal or a Group Mb metal oxide at a reaction temperature ranging from about 50° C. to about 125° C., wherein the molar ratio of isobutylene to phenol ranges from about 0.5:1 to about 3:1.

The desired tert-butyl phenol is typically a 2,6-di-tert-butyl phenol or ortho-tert-butyl phenol. However, other tert-butyl phenols, such as 2,4,6-tri-tert-butyl phenol are also useful products. Additionally, other tert-butyl phenols that are not directly produced from the initial reaction can be prepared by transalkylating the 2,6-di-tert-butyl phenol or ortho-tert-butyl phenol through means known in the art. See, for example, U.S. Pat. No. 5,399,786, herein incorporated by reference in its entirety, which discloses various transalkylation reactions. 2,6-di-tert-butyl phenol and/or ortho-tert-butyl phenol, for instance, can be transalkylated under well-known conditions to form compounds such as para-tert-butyl phenol, 2,4-di-tert-butyl phenol, or other butyl phenols known in the art.

Reacting a phenol or substituted phenol with the isobutylene in the $C_4$ raffinate stream produces the tert-butyl phenol, a reaction well understood in the art. Preferably at least about 80% of the available phenol or substituted phenol reacts with the isobutylene in forming the desired tert-butyl phenol. While phenol is the preferred reactant, various other substituted phenols may be used to produce other desired tert-butyl phenols, provided that the substituent in the substituted phenol does not otherwise interfere with the favored reaction.

A sufficient amount of isobutylene needs to be present in the $C_4$ raffinate stream in order to react with the phenol or substituted phenol. A typical isobutylene-containing $C_4$ raffinate stream contains anywhere from 35-95% isobutylene. For instance, $C_4$ raffinate streams may contain at least 75% isobutylene. Generally, the higher the percentage of isobutylene in the $C_4$ raffinate stream, the more preferable; but smaller amounts of isobutylene, even below 35% are acceptable and sufficient to run the reaction.

The reaction conditions, specifically the reaction temperature and the molar ratio of isobutylene to phenol (or substituted phenol) enable the selective reaction of isobutylene and phenol to produce a tert-butyl phenol that is substantially free of impurities and produced at high yields. Reaction temperatures range from about 50° C. to about 150° C., for instance from about 70° C. to about 130° C., from about 50° C. to about 125° C., from about 70° C. to about 125° C., or from 90° C. to 121° C. The use of controlled reaction temperature heat-up and cool-down ramps can be used, as they provide a good balance of reaction thermodynamics and kinetics to achieve a high level of selectivity and conversion in a relatively short amount of reaction time. Isothermal reactions run at higher reaction temperatures may also be used, but typically give poorer selectivity. Likewise, isothermal reactions run at lower reaction temperatures may be used, but require significantly longer reaction times. Pressures typically range from 0 to 500 psig. The reaction may be run in a batch mode, continuous mode, stirred-tank reactor, continuous stirred-tank reactor, fixed-bed reactor, fluidized-bed reactor, or other means known in the art.

Depending on the desired tert-butyl phenol, the molar ratio of isobutylene to phenol ranges can change. If the desired product is ortho-tert-butyl phenol, the ratio of isobutylene to phenol typically ranges from about 0.5:1 to about 1.5:1; if the desired product is 2,6-di-tert-butyl phenol, the ratio of isobutylene to phenol typically ranges from about 1.8:1 to about 2.8:1; and if the desired product is co-product of ortho-tert-butyl phenol and 2,6-di-tert-butyl phenol, the ratio of isobutylene to phenol typically ranges from about 1.3:1 to about 1.8:1. However, various other molar ranges with the molar range of 0.5:1-3:1, for instance 0.5:1-2.5:1 may be used for each desired product.

Any Group IIIb metal or Group IIIb metal oxide may be used as a catalyst in the reaction. A suitable Group IIIb metal is aluminum and a suitable Group IIIb metal oxide is an aluminum oxide. The Group IIIb metal and Group IIIb metal oxide may be used separately or together. Gamma-alumina may be used as the aluminum oxide catalyst. The gamma-alumina may be in the form of a powder, an extrudate, or other solid form.

The $C_4$ raffinate stream may also contain impurities, such as isobutane, n-butane, 1-butene, and 2-butene. In fact, most naturally occurring $C_4$ raffinate streams produced from naphtha streams contain hydrocarbon impurities ranging from $C_1$ to $C_5$. Butenes react with phenol to form undesirable sec-butyl phenols, among other products. While the impurities in the $C_4$ raffinate stream are not desirable, the cost savings of being able to react a phenol directly with a $C_4$ raffinate stream containing impurities—without having to conduct the additional step of either removing the impurities and forming a "pure" isobutylene or introducing another step to form an intermediate—can be significant.

Pure, or substantially pure, isobutylene can be obtained from the $C_4$ raffinate stream, but it is an expensive process. The more common approach, in conventional systems, is to introduce an alcohol, such as methanol or amyl alcohol, into the $C_4$ raffinate stream to form alkyl-tert-butyl ethers as intermediate products. The alkyl-tert-butyl ethers, for instance methyl-tert-butyl ether or methyl-tert-amyl ether, can then be reacted to form the desired mono-alkyl-phenols or di-alkyl-phenols. However, this process also adds additional steps, additional expenses, and creates various unwanted byproducts.

These additional steps can be avoided. Accordingly, an embodiment of the invention relates to an alcohol-free process for producing a tert-butyl phenol directly from an isobutylene-containing $C_4$ raffinate stream, the method comprising directly reacting the isobutylene-containing $C_4$ raffinate stream with a phenol to produce the tert-butyl phenol, wherein the reaction process avoids an intermediate step of introducing an alcohol into the $C_4$ raffinate stream. Another embodiment of the invention relates to a process for producing a tert-butyl phenol directly from an isobutylene-containing $C_4$ raffinate stream without forming an alkyl-tert-butyl ether as an intermediate, the method comprising directly reacting the isobutylene-containing $C_4$ raffinate stream with a phenol to produce the tert-butyl phenol, wherein the reaction proceeds without an intermediate step of forming an alkyl-tert-butyl ether.

When forming tert-butyl phenols, it is desirable for the phenol or substituted phenol to react with the isobutylene, but not react with the butenes. The reaction conditions noted above enable this type of selective reaction. Thus, the reaction is able to proceed in a manner where less than 3% of the 1-butene and 2-butene present in the $C_4$ raffinate stream react with the phenol or substituted phenol. In other embodiments, less than 2% of the 1-butene and 2-butene react with the phenol or substituted phenol; or less than 1% of the 1-butene and 2-butene react with the phenol or substituted phenol.

In this regard, an embodiment of the invention relates to a process for producing a tert-butyl phenol, comprising reacting a phenol with a $C_4$ raffinate stream containing (a) isobutylene, and (b) 1-butene and/or 2-butene under reaction conditions that selectively react the isobutylene with the phenol to produce the tert-butyl phenol without substantially reacting the 1-butene or 2-butene with the phenol.

Ortho-tert-butyl phenol is one of the desired tert-butyl phenols produced by the above-described reaction conditions. An embodiment of the invention is thus directed towards a process for producing ortho-tert-butyl phenol, comprising reacting an isobutylene-containing $C_4$ raffinate stream with a phenol in the presence of an aluminum oxide catalyst. When producing ortho-tert-butyl phenol, the reaction temperature preferably ranges from about 150° C. to about 200° C., such as from about 160° C. to about 180° C.; and the molar ratio of isobutylene to phenol preferably ranges from about 0.5:1 to about 1.5:1, such as from about 0.9:1 to about 1.1:1. The aluminum oxide catalyst can be a gamma-alumina that is in a solid form, such as a powder or an extrudate.

2,6-di-tert-butyl phenol is another tert-butyl phenol that can be produced by the above-described reaction conditions. An embodiment of the invention is thus directed towards a process for producing 2,6-di-tert-butyl phenol, comprising reacting an isobutylene-containing $C_4$ raffinate stream with ortho-tert-butyl phenol in the presence of aluminum or aluminum trisphenoxide. When producing 2,6-di-tert-butyl phenol, the reaction temperatures preferably range from about 0° C. to about 30° C., for instance from about 10° C. to about 20° C.; and the molar ratio of isobutylene to ortho-tert-butyl phenol preferably ranges from about 0.5:1 to about 2.0:1, such as from about 0.8:1 to about 1.2:1. The reaction typically takes place under pressure ranging from 0 to 50 psig.

Aluminum trisphenoxide may be added directly into the reaction or it may be formed during the reaction. For instance, the aluminum trisphenoxide may be formed by the reaction of a trialkyl aluminum with ortho-tert-butyl phenol, or by the reaction of aluminum metal with ortho-t-butyl phenol, which is typically the most economic means of forming aluminum trisphenoxide.

A separate embodiment of this invention relates to a composition comprising one or more tert-butyl phenols containing less than 0.5% by weight of sec-butyl phenols, wherein the composition is prepared by directly reacting a phenol with a $C_4$ raffinate stream containing (a) isobutylene and (b) 1-butene and/or 2-butene. Sec-butyl phenols are the undesirable product that forms when the butenes in the $C_4$ raffinate stream react with phenol. Limiting the amount of sec-butyl phenols is one way of enabling the desired tert-butyl phenols to be substantially pure, requiring fewer or no purification steps. High purity tert-butyl phenols can be economically purified by distillation or melt crystallization. However, when higher amounts of sec-butylphenol contaminants are present with the tert-butyl phenols, it becomes difficult to purify from the desired tert-butyl phenols, even using expensive processes like solvent crystallization. Thus, the tert-butyl phenol composition contains less than 0.5% by weight of sec-butyl phenols; for instance, less than 0.1% by weight of sec-butyl phenols, or less than 0.05% by weight of sec-butyl phenols.

The following examples are intended to illustrate the invention. These examples should not be used to limit the scope of the invention, which is defined by the claims.

EXAMPLES

Example 1

112.3 g of phenol that was pre-dried followed by dissolving 0.3% Al was charged to an autoclave. A raffinate-3 stream was charged into the reactor at a temperature of 118° C. at a rate of 3 g/minute for 60 minutes. The isobutylene content in the raffinate-3 stream was 87% with 12% isobutane and 0.5% n-butane. The butene content in the raffinate-3 stream was 0.3%. The temperature was lowered to 70° C. at the rate of 1° C./minute after 3 hours. The temperature was held at 70° C. for the remainder of the reaction. The total reaction time was 5 hours. The 2,6-di-tert-butyl phenol ("2,6-DTBP") yield in the crude product at the end of 5 hours was 76%. The final crude product had a 2,6-DTBP yield of 76%. The isobutylene to phenol mole ratio in this experiment was 2.06:1.

Example 2

A synthetic raffinate stream prepared by mixing pure isobutylene and pure isobutane was used for the following experiments. In this example, an experiment similar to example 1 was conducted, except using a synthetic raffinate stream containing 90% isobutylene and 10% isobutane. The reaction temperature was set at 118° C. for 2.5 hours and then lowered to 70° C. The 2,6-DTBP yield of the crude product at the end of 5 hours was 77%. The isobutylene to phenol mole ratio in this experiment was 2.23:1.

Example 3

This example was run in accordance with example 2, but using a synthetic raffinate stream containing 85% isobutylene and 15% isobutene. This gave a 2,6-DTBP yield of 77% at the end of 5 hours. The isobutylene to phenol mole ratio in this experiment was 2.11:1.

Example 4

This example was run in accordance with example 2, but using a synthetic raffinate stream containing 80% isobutylene and 20% isobutane gave a 2,6-DTBP yield of 76% at the end of 5 hours. Isobutylene to phenol mole ratio in this experiment was 2.02.

Example 5

129 grams of dry phenol was reacted with a synthetic raffinate stream containing 78.5% isobutylene, 1.1% 1-butene, and 20.4% isobutane using 0.3% Al catalyst. The initial reaction temperature was 90° C. The synthetic raffinate was charged into the reactor at the rate of 4 g/minute for the first thirty two minutes. Temperature was raised to 121° C. at the rate of 1.1° C./minute after 20 minutes of raffinate addition. The temperature was held steady at 121° C. for 65 minutes before cooling the reaction to 90° C. at the rate of 1° C./minute. The raffinate containing isobutylene was then added at the start of the cool down period at the rate of 4 g/minute for 20 minutes. The temperature was held at 90° C. for the remainder of the reaction. The total reaction time was 5 hours. The mole ratio of isobutylene to phenol in this example was 2.25:1. The final crude product had a 2,6-DTBP yield of 83.2%. The amount of 2-sec-6-tert-butylphenol was 0.03%, representing the reaction of 0.94% of the 1-butene in the initial raffinate.

Example 6

Comparative Example

A synthetic raffinate stream containing 79% isobutylene, 1% 1-butene, and 20% isobutane was added to 127 g of pre-dried phenol that had 0.3% dissolved Al. The reaction temperature was maintained at 130° C. for the entire duration of the reaction. The raffinate was added at the rate of 4 g/minute for 35 minutes. The reaction was held at 130° C. for 40 minutes followed by a vent step to relieve pressure and unreacted raffinate. More raffinate was added for additional 35 minutes at the rate of 4 g/minute. The isobutylene to phenol mole ratio based on the amount of isobutylene added to the reactor was 2.83:1. The yield of 2,6-DTBP in the crude product at the end of 5 hours was 58.36%. The amount of 2-sec-6-tert-butylphenol was 0.07%, representing the reaction of 3.9% of the 1-butene in the initial raffinate.

Example 7

Comparative Example

This example was run in accordance with example 6, except as noted below. The temperature was changed from 130° C. to 150° C. 101 g of phenol was used instead of 127 g to accommodate for the higher pressure that would be generated due to the higher temperature. Raffinate was added at the rate of 3 g/minute for 45 minutes. After holding the reaction for half hour at 150° C. and venting the reactor once, additional raffinate was added for 20 minutes at the rate of 3 g/minute. The final mole ratio of isobutylene to phenol based on the amount of isobutylene added to the reactor was 2.6:1. The yield of 2,6-DTBP in the crude product at the end of 5 hours was 61%. The amount of 2-sec-6-tert-butylphenol was 0.06%, representing the reaction of 3.9% of the 1-butene in the initial raffinate.

Example 8

Comparative Example

This example was run in accordance with example 7, except the temperature was changed from 150° C. to 170° C. The yield of 2,6-DTBP in the crude product at the end of 5 hours was 27%. The amount of 2-sec-6-tert-butylphenol was 0.20%, representing the reaction of 19.6% of the 1-butene in the initial raffinate.

Example 9

150 g of OTBP that was pre-dried followed by dissolving 5.6 g of triethylaluminum was charged in a jacketed glass pressure reactor that was connected to a cooling bath. The bath temperature was set at 20° C. Synthetic raffinate containing 79% isobutylene, 19.5% isobutene, and 1.5% 1-butene was charged 1 g/minute for 70 minutes. The temperature during isobutylene addition (during the first hour of the reaction) was 35° C. due to exotherm associated with the reaction. The reaction temperature after the first hour through the end of the reaction was 20° C. The yield of 2,6-DTBP in the crude product at the end of 4 hours was 89%. The mole ratio of isobutylene to OTBP was 1:1. The maximum pressure attained during the reaction was 25 psig.

Example 10

This example was run in accordance with example 9, except that the raffinate was charged at the rate of 0.33 g/minute and the reactor temperature was maintained at 10° C. The yield of 2,6-DTBP in the crude product at the end of 4 hours was 93%. The maximum pressure attained during the reaction was 15 psig.

Example 11

This example was run in accordance with example 10, except that the reactor temperature was maintained at 5° C. The yield of 2,6-DTBP in the crude product at the end of 4 hours was 80%. The maximum pressure attained during the reaction was 12 psig.

Example 12

105 g of phenol and 5.3 g of aluminum oxide catalyst that was calcined in air at a temperature of 450° C. was charged in an autoclave and heated to 150° C. A raffinate stream containing 80% isobutylene, 18.7% isobutane and 1.4% 1-butene was then charged over a period of 3.5 hours. The amount of raffinate charged was 75 g with a isobutylene to phenol mole ratio of 0.95:1. The yield of OTBP at the end of 7 hours was 49%. The amount of 1-butene in the feed that reacted to form 2-sec-butylphenol was 1.3%.

Example 13 (Comparative Example)

105 g of phenol and 5.0 g of aluminum oxide catalyst that was calcined in air at a temperature of 450° C. was charged in an autoclave and heated to 220° C. A raffinate stream containing 82.4% isobutylene, 1.3% 1-butene, and 16.3% isobutane was then charged over a period of 3 hours. The amount of raffinate charged was 70 g with an isobutylene to phenol mole ratio of 1.13:1. The yield of OTBP at the end of 6 hours was 50.41%, down from 52% at the 5-hour mark. The amount of 1-butene in the feed that reacted to form 2-sec-butylphenol and 2-sec-butyl-4-tert-butylphenol was 44.5%. The amount of the two sec-butylphenol impurities (2-sec-butylphenol and 2-sec-butyl-4-tert-butylphenol) were 0.44 area percent and 0.15%, respectively.

Example 14

106 grams of crude 2,6-di-tert-butylphenol containing 75.4% 2,6-di-tert-butylphenol and 0.43% 2-sec-6-tert-di-butylphenol was transalkylated with phenol using 5 grams of Dowex® 2030 ion exchange resin (DR-2030; a styrenic plastic bead functionalized with sulfonic acid groups) at 75° C. for 5 hours to produce 75.4% 2,4-di-tert-butylphenol containing 0.3% 2-sec-4-tert-di-butylphenol and no measurable amounts of 2-sec-6-tert-di-butylphenol.

This example illustrates the use of a crude 2,6-di-tert-butylphenol made from a raffinate, in a transalkylation reaction to produce 2,4-di-tert-butylphenol. High purity 2,4-di-tert-butylphenol can be further made by fractional distillation by procedures known to one skilled in the art.

Example 15 (Comparative)

A synthetic raffinate containing 78.3% isobutylene, 21% isobutane, 0.54% 1-butene was used for the butylation of phenol using DR-2030 as the catalyst. Temperature of the reaction was set at 80° C. 204 g of the synthetic raffinate was added over a period of 3 hours. Progress of the reaction was monitored by analyzing periodic samples by GC. At the end of 5 hours the area percent yield of 2,4-DTBP was 73.8%. The amount of 2-sec-butyl-4-tert-butylphenol was 0.49% and the amount of 2-tert-butyl-4-sec-butylphenol was 0.03%. The amount of 1-butene in the feed that reacted to form 2s4t and 2t4s was 30%.

We claim:

1. A process for producing 2,6-di-tert-butyl phenol, comprising reacting a phenol with a $C_4$ raffinate stream containing (a) isobutylene, and (b) 1-butene and/or 2-butene under reaction conditions, including a reaction temperature ranging from about 50° C. to about 150° C. and under pressure ranging from 0 to 500 psig, that selectively react the isobutylene with the phenol to produce the 2,6-di-tert-butyl phenol without substantially reacting the 1-butene or 2-butene with the phenol, wherein the molar ratio of isobutylene to phenol ranges from about 0.5:1 to about 3:1, and wherein the phenol reacts with the isobutylene to yield at least 76% by weight of the 2,6-di-tert-butyl phenol.

2. The process of claim 1, wherein less than 1% by weight of the 1-butene and 2-butene present in the $C_4$ raffinate stream is reacted with the phenol.

3. The process of claim 1, wherein at least about 80% by weight of the phenol reacts with the isobutylene.

4. The process of claim 1, wherein the process produces less than 0.1% by weight of sec-butyl phenols.

5. The process of claim 1, wherein the isobutylene-containing $C_4$ raffinate stream is directly reacted with a phenol, the reaction proceeding without an intermediate step of forming an alkyl-tert-butyl ether.

6. The process of claim 5, wherein the alkyl-tert-butyl ether is methyl-tert-butyl ether or methyl-tert-amyl ether.

7. The process of claim 1, wherein the isobutylene-containing $C_4$ raffinate stream is directly reacted with a phenol, the reaction proceeding without an intermediate step of introducing an alcohol into the $C_4$ raffinate stream.

8. The process of claim 7, wherein the alcohol is methanol or amyl alcohol.

9. The process of claim 1, further comprising the step of transalkylating the 2,6-di-tert-butyl phenol to form a compound selected from the group consisting of para-tert-butyl phenol, 2,4-di-tert-butyl phenol, and a combination thereof.

10. The process of claim 1, wherein the isobutylene-containing C4 raffinate stream contains at least 75% by weight isobutylene.

11. The process of claim 1, wherein the isobutylene-containing $C_4$ raffinate stream is reacted with the phenol in the presence of aluminum.

12. The process of claim 1, wherein the phenol is an ortho-tert-butyl phenol.

13. The process of claim 12, wherein the isobutylene-containing $C_4$ raffinate stream is reacted with ortho-tert-butyl phenol in the presence of aluminum or aluminum trisphenoxide at a reaction temperature ranging from about 10° C. to about 20° C. and under pressure ranging from 0 to 50 psig, wherein the molar ratio of isobutylene to ortho-tert-butyl phenol ranges from about 0.8:1 to about 1.2:1.

14. The process of claim 13, wherein the aluminum trisphenoxide is formed by the reaction of a trialkyl aluminum with ortho-tert-butyl phenol.

15. The process of claim 1, wherein the reaction is run in a batch mode, continuous mode, stirred-tank reactor, continuous stirred-tank reactor, fixed-bed reactor, or fluidized bed reactor.

16. A process for producing 2,6-di-tert-butyl phenol, comprising reacting a phenol with a $C_4$ raffinate stream containing (a) isobutylene, and (b) 1-butene and/or 2-butene under reaction conditions, including a reaction temperature ranging from about 70° C. to about 130° C., that selectively react the isobutylene with the phenol to produce the 2,6-di-tert-butyl phenol without substantially reacting the 1-butene or 2-butene with the phenol, wherein the molar ratio of isobutylene to phenol ranges from about 1.8:1 to about 2.8:1.

17. The process of claim 16, wherein less than 1% by weight of the 1-butene and 2-butene present in the $C_4$ raffinate stream is reacted with the phenol.

18. The process of claim 16, wherein at least about 80% by weight of the phenol reacts with the isobutylene.

19. The process of claim 16, wherein the process produces less than 0.1% by weight of sec-butyl phenols.

20. The process of claim 16, wherein the isobutylene-containing $C_4$ raffinate stream is directly reacted with a phenol, the reaction proceeding without an intermediate step of forming an alkyl-tert-butyl ether.

21. The process of claim 20, wherein the alkyl-tert-butyl ether is methyl-tert-butyl ether or methyl-tert-amyl ether.

22. The process of claim 16, wherein the isobutylene-containing $C_4$ raffinate stream is directly reacted with a phenol, the reaction proceeding without an intermediate step of introducing an alcohol into the $C_4$ raffinate stream.

23. The process of claim 22, wherein the alcohol is methanol or amyl alcohol.

24. The process of claim 16, wherein the isobutylene-containing $C_4$ raffinate stream contains at least 75% by weight isobutylene.

25. The process of claim 16, wherein the isobutylene-containing $C_4$ raffinate stream is reacted with the phenol in the presence of aluminum.

* * * * *